(12) United States Patent
Nakamura et al.

(10) Patent No.: US 12,733,797 B2
(45) Date of Patent: Sep. 15, 2026

(54) RIGIDITY CONTROL APPARATUS, ENDOSCOPE SYSTEM, AND RIGIDITY CONTROL METHOD

(71) Applicant: OLYMPUS MEDICAL SYSTEMS CORP., Tokyo (JP)

(72) Inventors: Sho Nakamura, Orefield, PA (US); Sayuri Yamamoto, Hino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 286 days.

(21) Appl. No.: 18/244,584

(22) Filed: Sep. 11, 2023

(65) Prior Publication Data

US 2023/0414077 A1 Dec. 28, 2023

Related U.S. Application Data

(63) Continuation of application No. PCT/JP2021/010710, filed on Mar. 16, 2021.

(51) Int. Cl.
*A61B 1/005* (2006.01)
*B25J 19/06* (2006.01)

(52) U.S. Cl.
CPC .......... *A61B 1/0051* (2013.01); *A61B 1/0058* (2013.01); *A61B 1/009* (2022.02); *B25J 19/068* (2013.01)

(58) Field of Classification Search
CPC . A61B 1/0051; A61B 1/00078; A61B 1/0058; A61B 1/009
See application file for complete search history.

(56) References Cited

U.S. PATENT DOCUMENTS

| | | | | | |
|---|---|---|---|---|---|
| 4,884,557 | A * | 12/1989 | Takehana | A61B 1/0058 | 600/145 |
| 4,930,494 | A * | 6/1990 | Takehana | F03G 7/066 | 600/145 |
| 5,624,380 | A * | 4/1997 | Takayama | A61B 1/0058 | 600/141 |
| 2008/0097159 | A1 | 4/2008 | Ishiguro | | |
| 2009/0079821 | A1 | 3/2009 | Bousquet et al. | | |

(Continued)

FOREIGN PATENT DOCUMENTS

| | | |
|---|---|---|
| CN | 101198370 A | 6/2008 |
| CN | 101416868 A | 4/2009 |

(Continued)

OTHER PUBLICATIONS

International Search Report dated Jun. 8, 2021 received in PCT/JP2021/010710.

*Primary Examiner* — Aaron B Fairchild
(74) *Attorney, Agent, or Firm* — Scully, Scott, Murphy & Presser, P.C.

(57) ABSTRACT

A rigidity control apparatus includes a processor and controls a variable-rigidity apparatus. The variable-rigidity apparatus includes a variable-rigidity member, flexural rigidity of which increases when the variable-rigidity member is heated, and a heater configured to be able to heat the variable-rigidity member. The processor calculates information about temperature of the heater, and estimates information about temperature of the variable-rigidity member based on the information about the temperature of the heater.

13 Claims, 6 Drawing Sheets

(56) References Cited

U.S. PATENT DOCUMENTS

| | | | | |
|---|---|---|---|---|
| 2009/0303619 | A1* | 12/2009 | Iwasaki | G02B 23/243<br>310/306 |
| 2018/0080437 | A1* | 3/2018 | Morishima | A61B 1/0053 |
| 2018/0266402 | A1 | 9/2018 | Takahashi | |
| 2018/0289925 | A1 | 10/2018 | Palmer et al. | |
| 2019/0046008 | A1 | 2/2019 | Morishima | |
| 2019/0046010 | A1 | 2/2019 | Tojo et al. | |

FOREIGN PATENT DOCUMENTS

| | | | |
|---|---|---|---|
| CN | 109068939 | A | 12/2018 |
| JP | H05-42100 | A | 2/1993 |
| JP | 2020-137089 | A | 8/2020 |
| WO | 2016189683 | A1 | 12/2016 |
| WO | 2017179126 | A1 | 10/2017 |
| WO | 2018/191259 | A1 | 10/2018 |
| WO | 2018189888 | A1 | 10/2018 |

* cited by examiner 2
3
11
11A
11B
11C
12
12A
12B
13
13A
14
20
21
22
23

FIG. 2

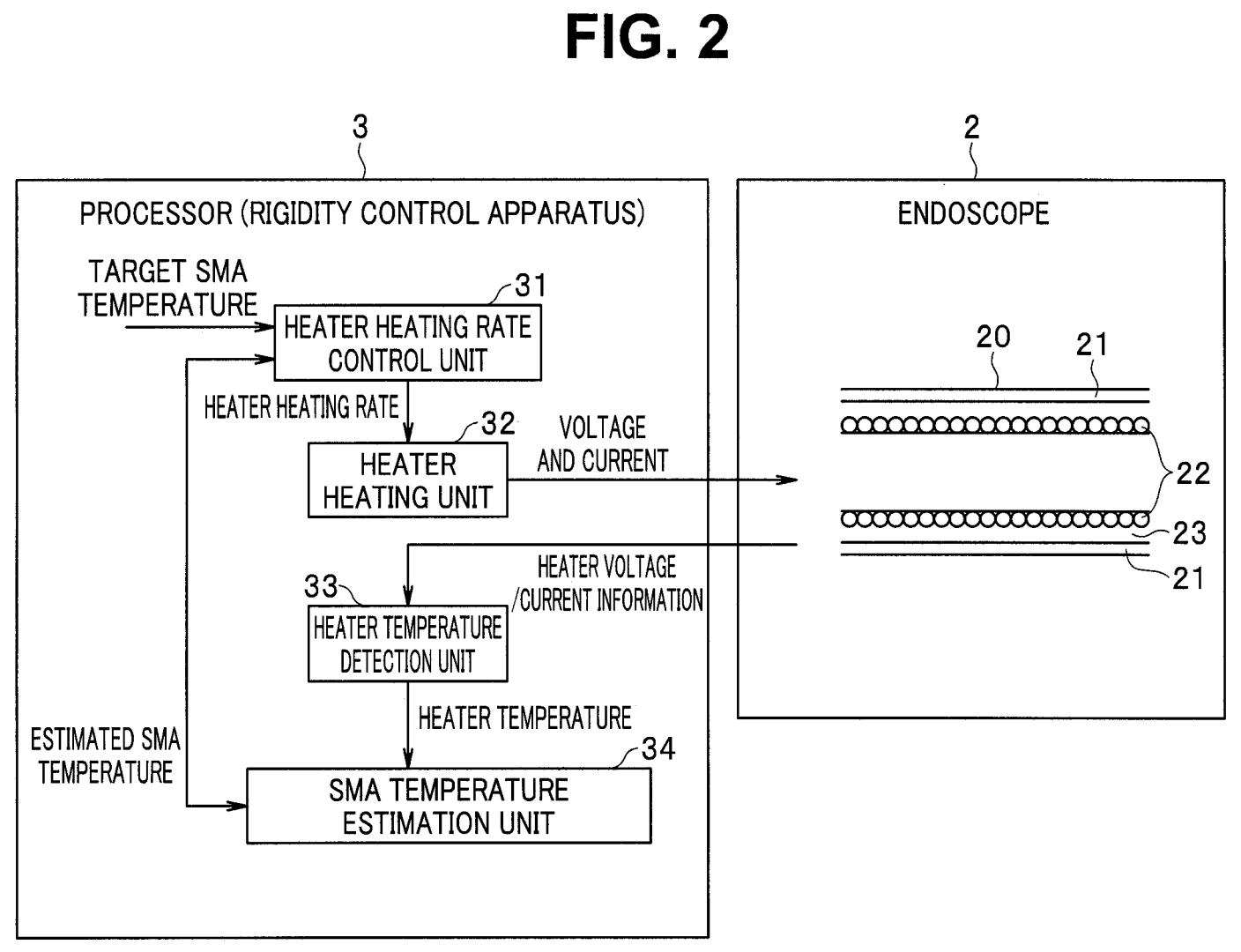

2
ENDOSCOPE
20
21
22
23
21

3
PROCESSOR (RIGIDITY CONTROL APPARATUS)
TARGET SMA TEMPERATURE
31
HEATER HEATING RATE CONTROL UNIT
HEATER HEATING RATE
32
HEATER HEATING UNIT
VOLTAGE AND CURRENT
HEATER VOLTAGE /CURRENT INFORMATION
33
HEATER TEMPERATURE DETECTION UNIT
HEATER TEMPERATURE
34
SMA TEMPERATURE ESTIMATION UNIT
ESTIMATED SMA TEMPERATURE

GAIN SETTING TABLE

| ESTIMATED SMA TEATURE AT HEATING START TIME | GAIN | TIME CONSTANT |
|---|---|---|
| 10° ~ 30° | 0.94 | 1 |
| 30° ~ 50° | 1.01 | 1 |
| 50° ~ 70° | 1.04 | 1 |

FIG. 7

TIME CONSTANT SETTING TABLE

| ESTIMATED SMA TEMPERATURE | HEATING STATUS OF SMA | TIME CONSTANT |
|---|---|---|
| 10° ～ 45° | HEATED | 1 |
| 45° ～ 53° | HEATED | 1.4 |
| 53° ～ 90° | HEATED | 1 |
| 90° ～ 40° | DISSIPATING | 1 |
| 40° ～ 32° | DISSIPATING | 1.4 |
| 32° ～ 10° | DISSIPATING | 1 |

RIGIDITY CONTROL APPARATUS, ENDOSCOPE SYSTEM, AND RIGIDITY CONTROL METHOD

CROSS REFERENCE TO RELATED APPLICATION

This application is a continuation application of PCT/JP2021/010710 filed on Mar. 16, 2021, the entire contents of which are incorporated herein by this reference.

BACKGROUND OF THE INVENTION

1. Field of the Invention

The present invention relates to a rigidity control apparatus that includes a variable-rigidity apparatus configured to change rigidity of an endoscope insertion portion and controls the variable-rigidity apparatus as well as to an endoscope system and a rigidity control method for the rigidity control apparatus.

2. Description of the Related Art

Conventionally, various systems have been known as variable-rigidity apparatuses configured to change rigidity of an endoscope insertion portion. As a system of the variable-rigidity apparatus, a system that increases rigidity by heating a shape-memory alloy (SMA) member with a heater coil is known. For example, International Publication No. 2018/189888 discloses a configuration in which a shape-memory alloy (SMA) member is formed into a pipe shape and a heating element (heater coil) is placed coaxially with the SMA pipe.

As a rigidity control method for a shape-memory alloy (SMA) member, International Publication No. 2016/189683 discloses a technique for measuring heater coil temperature based on measurement of heater coil electrical resistance and then calculating (estimating) rigidity of the shape-memory alloy (SMA) member based on the heater coil temperature.

SUMMARY OF THE INVENTION

A rigidity control apparatus according to one aspect of the present invention includes a processor configured to control a variable-rigidity apparatus, the variable-rigidity apparatus including a variable-rigidity member, flexural rigidity of which increases when the variable-rigidity member is heated, and a heater configured to be able to heat the variable-rigidity member, wherein the processor: calculates information about temperature of the heater, and estimates information about temperature of the variable-rigidity member based on the information about the temperature of the heater.

An endoscope system according to one aspect of the present invention includes: an endoscope; and a rigidity control apparatus equipped with a processor, the endoscope including an insertion portion and a variable-rigidity apparatus, the variable-rigidity apparatus including a variable-rigidity member mounted on the insertion portion and configured to increase in flexural rigidity when heated, and a heater mounted on the insertion portion and configured to be able to heat the variable-rigidity member, wherein the processor calculates temperature of the heater and estimates temperature of the variable-rigidity member based on the temperature of the heater.

A rigidity control method according to one aspect of the present invention is a rigidity control method for controlling a variable-rigidity apparatus that includes a variable-rigidity member configured to increase in flexural rigidity when heated, and a heater configured to be able to heat the variable-rigidity member, the method including: calculating information about temperature of the heater; and estimating temperature of the variable-rigidity member based on the information about the temperature of the heater.

BRIEF DESCRIPTION OF THE DRAWINGS

FIG. 2 is a block diagram showing a configuration of main part of the rigidity control apparatus according to the first embodiment and a configuration of the variable-rigidity apparatus in an endoscope insertion portion;

FIG. 7 is a table showing a time constant setting table used for the rigidity control apparatus according to the third embodiment.

DETAILED DESCRIPTION OF THE PREFERRED EMBODIMENTS

Embodiments of the present invention will be described below using the drawings.

First Embodiment

Figure 1:
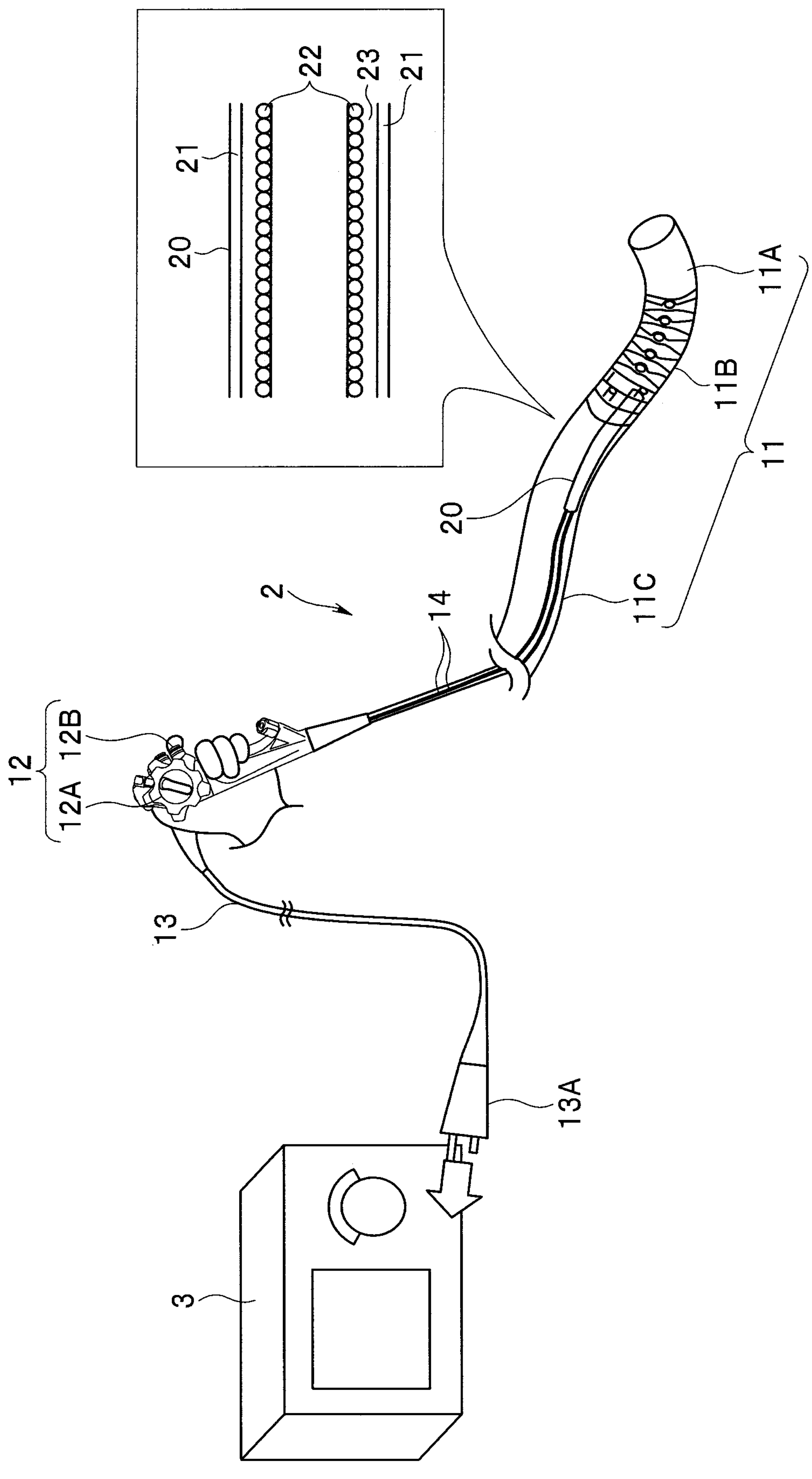
FIG. 1 is an external perspective view of principal part showing a configuration of an endoscope system that includes a rigidity control apparatus according to a first embodiment of the present invention and an endoscope equipped with a variable-rigidity apparatus controlled by the rigidity control apparatus.

FIG. 1 is an external perspective view of principal part showing a configuration of an endoscope system that includes a rigidity control apparatus according to a first embodiment of the present invention and an endoscope equipped with a variable-rigidity apparatus controlled by the rigidity control apparatus, and FIG. 2 is a block diagram showing a configuration of main part of the rigidity control apparatus according to the first embodiment and a configuration of the variable-rigidity apparatus in an endoscope insertion portion.

As shown in FIGS. 1 and 2, an endoscope system 1 according to the first embodiment of the present invention mainly includes an endoscope 2 inserted into a subject and used to pick up endoscopic images in a body cavity, and a control apparatus 3 connected to the endoscope 2 and configured to apply predetermined image processing to acquired endoscopic images and output the resulting endoscopic images to the outside.

The endoscope 2 includes an insertion portion 11 inserted into the subject, an operation portion 12 provided on a proximal end side of the insertion portion 11, and a universal cord 13 extended from the operation portion 12. The endoscope 2 is configured to be detachably connected to the control apparatus 3 via a scope connector 13A provided in an end portion of the universal cord 13.

In the present embodiment, the control apparatus 3 contains a non-illustrated light source device. A light guide (not shown) for use to transmit illuminating light supplied from the light source device as well as a predetermined electric cable 14 extended from the control apparatus 3 are disposed inside the insertion portion 11, the operation portion 12, and the universal cord 13.

The insertion portion 11 has flexibility and an elongated shape. Starting from a distal end side, the insertion portion 11 includes a rigid, distal end portion 11A, a bending portion 11B configured to be bendable, and a long, flexible tubular portion 11C having flexibility.

The distal end portion 11A is provided with an illuminating window (not shown) for use to emit illuminating light to an object, where the illuminating light is transmitted through the light guide provided inside the insertion portion 11. The distal end portion 11A is provided also with an image pickup unit (not shown) configured to operate in response to an image pickup control signal supplied from the control apparatus 3 and pick up an image of the object illuminated by the illuminating light emitted through the illuminating window and output an image pickup signal. The image pickup unit includes an image sensor such as a CMOS image sensor or CCD image sensor.

The bending portion 11B is configured to be bendable in response to operation of an angle knob 12A provided on the operation portion 12.

According to the present embodiment, although details will be described later, in a variable-rigidity range, which corresponds to a predetermined range from a proximal end portion of the bending portion 11B to a distal end portion of the flexible tubular portion 11C, a variable-rigidity apparatus 20 is provided in a longitudinal direction of the insertion portion 11, being configured to be able to change flexural rigidity of the variable-rigidity range under the control of the control apparatus 3 (rigidity control apparatus). A concrete configuration and the like of the variable-rigidity apparatus 20 will be described in detail later.

Note that hereinafter, for convenience of explanation, "flexural rigidity" will be abbreviated simply to "rigidity" as appropriate. In the present embodiment, it is sufficient that the variable-rigidity range described above covers at least part of the insertion portion 11.

The operation portion 12 is shaped to be gripped and operated by a user. The operation portion 12 is provided with the angle knob 12A configured to be operated to allow the bending portion 11B to be bent in four—upward, downward, left, right (UDLR)—directions intersecting a longitudinal axis of the insertion portion 11. The operation portion 12 is provided with one or more scope switches 12B capable of giving instructions according to user input operation.

<Variable-Rigidity Apparatus 20>

As shown in FIGS. 1 and 2, the variable-rigidity apparatus 20 is made up of an SMA pipe 21, a heater 22, and a thermally conductive member 23 and configured to be able to change flexural rigidity of the variable-rigidity range under the control of the control apparatus 3 (rigidity control apparatus).

The SMA pipe 21, which is formed of a shape-memory alloy (SMA) member exhibiting a small-diameter pipe shape, is a variable-rigidity member that increases in flexural rigidity when heated. The SMA pipe 21 according to the present embodiment is disposed in the longitudinal direction of the insertion portion 11 in a predetermined range from the proximal end portion of the bending portion 11B to the distal end portion of the flexible tubular portion 11C in the insertion portion 11 of the endoscope 2. Note that although the variable-rigidity member according to the present embodiment exhibits a small-diameter pipe shape, the shape of the variable-rigidity member is not limited to this, and variable-rigidity members of various shapes are available for use.

The heater 22 is made up of a heat coil disposed in a longitudinal direction in an inner diameter portion of the SMA pipe 21. The heat coil is formed by winding an electric conductor coaxially with an axis of the SMA pipe 21 into a substantially cylindrical shape, where the electric conductor, which has electrical conductivity, generates heat when energized by being supplied with electric power.

In the present embodiment, the heater 22 is placed on an inner side of the SMA pipe 21, which is the variable-rigidity member, and disposed in the longitudinal direction with an outer peripheral portion of the cylindrical coil substantially abutting the inner diameter portion of the SMA pipe 21.

In the present embodiment, the heater 22 is connected to a heater heating unit 32 of the control apparatus 3 and generates heat by being supplied with electric power from the heater heating unit 32. The heating of the heater 22 is designed to be controlled by a heater heating rate control unit 31 disposed likewise in the control apparatus 3. Heating control of the heater 22 will be described later.

When the heater 22 generates heat by being supplied with electric power, a resistance value of the heater 22 changes with temperature changes, and a voltage value and a current value on a power supply line connected to the heater 22 change accordingly. In the present embodiment, when the voltage value and the current value on the power supply line is measured, information about the resistance value of the heater 22 is fed back to the control apparatus 3, temperature of the heater 22 is detected from the information about the resistance value of the heater 22, and moreover, temperature of the SMA pipe 21 is estimated from the temperature of the heater 22. The detection of the heater temperature and the estimation of the temperature of the SMA pipe 21 will be described in detail later.

Note that a technique described in International Publication No. 2018/189888 may be used for the configurations of the SMA pipe 21 and the heater 22, but the present embodiment is characterized in that a space between the heater 22 and the SMA pipe 21 is filled with the thermally conductive member 23 not adopted by the technique described in International Publication No. 2018/189888.

As described above, the thermally conductive member 23 is a characteristic component adopted in the present embodiment and is made of thermally conductive material, thermal conductivity of which is at least higher than air. In the present embodiment, a clearance portion between the heater 22 and the inner diameter portion of the SMA pipe 21, which is the variable-rigidity member, is filled with the thermally conductive member 23, which serves a role of efficiently transmitting heat generated by the heater 22 to the SMA pipe 21.

In this way, by placing the thermally conductive member 23 between the SMA pipe 21, which is the shape-memory alloy (SMA) member, and the heater 22, which is the heater coil, the present embodiment achieves the effect of reducing a temperature difference between the shape-memory alloy member and the heater coil.

<Rigidity Control Apparatus (Control Apparatus 3)>

In the present embodiment, the control apparatus 3 has various publicly known functions of a so-called video processor (image processing apparatus), such as a function of applying predetermined image processing to endoscopic images acquired through connection to the endoscope 2 and outputting the resulting endoscopic images to the outside and a function of controlling the connected endoscope 2, but detailed description of the publicly known functions of the image processing apparatus will be omitted, and components having functions characteristic of the present embodiment will be described below.

FIG. 2 is a block diagram showing a configuration of main part of the control apparatus 3 serving as the rigidity control apparatus according to the present embodiment and a configuration of the variable-rigidity apparatus 20 in an endoscope insertion portion.

As shown in FIG. 2, the control apparatus 3 according to the present embodiment includes functions of the rigidity control apparatus configured to control the variable-rigidity apparatus 20 of the endoscope 2 in addition to including components related to a non-illustrated publicly known image processing functions.

Specifically, the control apparatus 3 includes the heater heating unit 32 connected to the variable-rigidity apparatus 20, the heater heating rate control unit 31 (heater control unit) configured to control the heater heating unit 32, a heater temperature detection unit 33 configured to detect the temperature of the heater 22 in the variable-rigidity apparatus 20, and an SMA temperature estimation unit 34 configured to estimate the temperature of the SMA pipe 21 based on the temperature of the heater 22 detected by the heater temperature detection unit 33.

When the endoscope 2 is connected to the control apparatus 3, the heater heating unit 32 supplies electric power to the heater 22 in the variable-rigidity apparatus 20 disposed in the endoscope 2 through the power supply line to cause the heater 22 to generate heat. In so doing, the heater heating unit 32 supplies the electric power under the control of the heater heating rate control unit 31 based on heater heating rate information acquired from the heater heating rate control unit 31.

The heater heating rate control unit 31 acquires a predetermined target SMA temperature, calculates a heater heating rate to apply electric power to the heater 22 based on the acquired target SMA temperature and an estimated SMA temperature acquired from the SMA temperature estimation unit 34, and transmits information about the heater heating rate to the heater heating unit 32.

Note that the heater heating rate control unit 31 also has a function to estimate rigidity of the SMA pipe 21 based on the estimated SMA temperature acquired from the SMA temperature estimation unit 34.

The heater temperature detection unit 33 acquires voltage/current information about the heater 22 from the endoscope 2. For example, the heater temperature detection unit 33 acquires information about a heater voltage by being connected to a signal line used to measure a voltage across the heater 22 and acquires a heater current by being connected to the power supply line used to supply electric power intended to heat the heater 22. Then, the heater temperature detection unit 33 successively acquires information about the resistance value of the heater 22 based on the acquired voltage/current information about the heater 22. Furthermore, the heater temperature of the heater 22 is calculated successively from a relational expression between the heater resistance value and the heater temperature.

The SMA temperature estimation unit 34 acquires information about the heater temperature of the heater 22 calculated by the heater temperature detection unit 33 and estimates the temperature (SMA temperature) of the SMA pipe 21 (hereinafter abbreviated to SMA in some cases), which is the shape-memory member. In so doing, the SMA temperature estimation unit 34 estimates the SMA temperature of the SMA pipe 21 based on a "heat conduction model" that takes into consideration respective thermal conductivity properties of "a member between the heater 22 and the SMA pipe 21," "the SMA pipe 21 itself." and the "surrounding environment of the SMA pipe 21" in addition to the acquired heater temperature information.

Note that in the present embodiment, the SMA temperature estimation unit 34 serves the function of a variable-rigidity member temperature estimation unit.

<Estimation of SMA Temperature by SMA Temperature Estimation Unit 34>

Next, description will be given of an SMA temperature estimation technique used by the SMA temperature estimation unit 34 serving the role of the variable-rigidity member temperature estimation unit.

The SMA temperature estimation unit 34 outputs information about the temperature of the SMA pipe 21 based on a function that has a gain in the temperature of the SMA pipe 21 with respect to the temperature of the heater 22 and a time constant regarding quickness of responses in temperature changes of the SMA pipe 21, where the function uses information about the temperature of the heater 22 calculated by the heater temperature detection unit 33 as an input value and outputs information about the temperature of the SMA pipe 21, which is the variable-rigidity member.

Specifically, based on an expression derived from a set heat conduction equation, the SMA temperature estimation unit 34 estimates the SMA temperature of the SMA pipe 21 using information about the temperature of the heater 22 as an input value.

<SMA Temperature Estimation Technique of SMA Temperature Estimation Unit 34 According to First Embodiment>

Concrete description will be given below of the SMA temperature estimation technique used by the SMA temperature estimation unit 34 according to the first embodiment.

In the first embodiment, by setting the heat conduction equation shown below and using the Laplace transform of the heat conduction equation as a linear transfer function, the heater temperature as input, and the estimated SMA temperature as output, the SMA temperature of the SMA pipe 21 is estimated.

Note that in the first embodiment, "gain" and "time constant" are fixed values.

[Heat Conduction Equation in First Embodiment]

$$mc\frac{dT_{MSA}}{dt} = \frac{k_K A_K}{D_K}(T_{HEATER} - T_{SMA}) - \frac{k_s A_s}{D_s}(T_{SMA} - T_e)$$

m: Mass of SMA [g],
c: Specific heat of SMA [J/g/K],
$T_{SMA}$: SMA temperature [K] (output value),
t: time [s],
$K_K$: Average thermal conductivity from heater coil to SMA (mainly conductive material),
$A_K$: Average surface area from heater coil to SMA (mainly conductive material),
$D_K$: Average thickness from heater coil to SMA (mainly conductive material),
$T_{HEATER}$: Heater temperature (input value),
$K_S$: Average thermal conductivity of surrounding environment of SMA (in-scope air space and in-scope components),
$A_S$: Surface area of SMA [m$^2$],
$D_S$: Average thickness to surrounding environment of SMA (in-scope air space and in-scope components).
$T_e$: Temperature [K] of surrounding environment of SMA (in-scope air space and in-scope components)

[Laplace Transform of Linear Transfer Function]

Figures 3, 4:
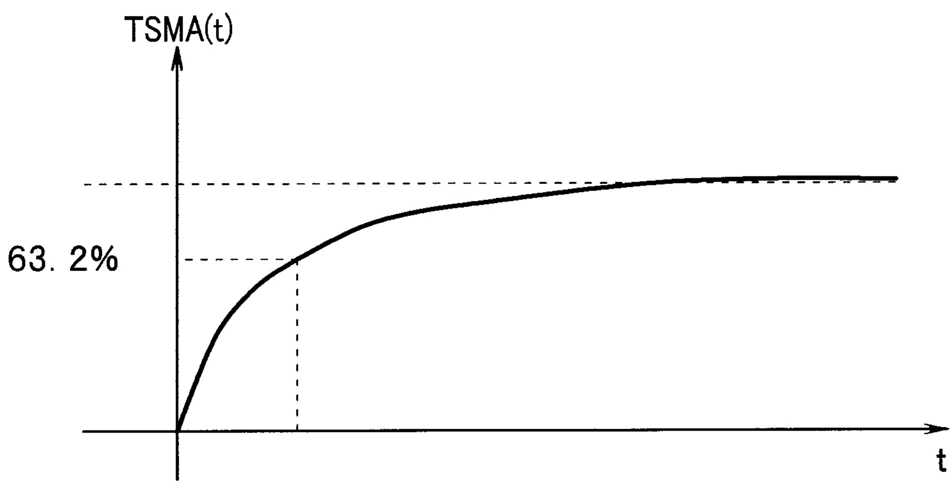
FIG. 3 is a graphical chart showing temperature rising characteristics of a shape-memory member found by a variable-rigidity member temperature estimation unit in the rigidity control apparatus according to the first embodiment.
FIG. 4 is a table showing a gain setting table used for a rigidity control apparatus according to a second embodiment of the present invention.

The linear transfer function resulting from the Laplace transform of the heat conduction equation is as follows.

$$\frac{T_{SMA}}{T_{HEATER}} = \frac{\frac{k_K A_K}{D_K}}{\frac{k_K A_K}{D_K} + \frac{k_s A_s}{D_s}}\left(1 + \frac{T_e}{T_{HEATER}}\right) \times \frac{1}{1 + \frac{mc}{\frac{k_K A_K}{D_K} + \frac{k_s A_s}{D_s}} s}$$

$$\text{Gain: } \frac{\frac{k_K A_K}{D_K}}{\frac{k_K A_K}{D_K} + \frac{k_s A_s}{D_s}}\left(1 + \frac{T_e}{T_{HEATER}}\right)$$

$$\text{Time constant: } \frac{mc}{\frac{k_K A_K}{D_K} + \frac{k_s A_s}{D_s}}$$

where "S" is a Laplace operator, which has a meaning of a time derivative, and the SMA temperature $T_{SMA}$, which is an output value, rises temporally smoothly as shown in FIG. 3.

As described above, in the first embodiment, "gain" and "time constant" are set as fixed values.

Here, when the heater temperature $T_{HEATER}$, which is an input value, is "1,"

$$T_{SMA}(t) = \text{Gain}\left(1 - e^{-\frac{t}{\tau}}\right)$$

$$\text{Gain (Gain)} = \frac{\frac{k_K A_K}{D_K}}{\frac{k_K A_K}{D_K} + \frac{k_s A_s}{D_s}}\left(1 + \frac{T_e}{T_{HEATER}}\right)$$

$$\text{Time constant } \tau = \frac{mc}{\frac{k_K A_K}{D_K} + \frac{k_s A_s}{D_s}}$$

"Gain" defines how many times higher the output (SMA temperature $T_{SMA}$) eventually becomes than the heater temperature, which is input. "Time constant" specifies the time at which the output reaches a value of 63.2% of the gain (see FIG. 3).

Note that the rigidity control apparatus according to the first embodiment may further include a shape detection unit configured to detect a shape of the insertion portion 11 of the endoscope 2, and a selection unit configured to select a heat conduction equation to be applied to calculations according to the detected shape from multiple different heat conduction equations. Clearances among components of the endoscope 2 may change with changes in a bend of the insertion portion 11, but the shape detection unit and the selection unit allow an optimum heat conduction equation to be selected by considering changes in the clearances. For example, a magnetic shape sensor may be used as the shape detection unit.

Effect of First Embodiment

As described above, by estimating the temperature of the shape-memory alloy member (SMA pipe 21), which is the variable-rigidity member making up the variable-rigidity apparatus, using the expression derived from the predetermined heat conduction equation and using temperature information about the heater 22 of the variable-rigidity apparatus as an input value, the rigidity control apparatus according to the first embodiment can further increase accuracy of rigidity control over the SMA pipe 21.

Second Embodiment

Next, a second embodiment of the present invention will be described.

A rigidity control apparatus according to the second embodiment is similar to the first embodiment in a basic configuration, and thus only differences will be described here. Note that both in terms of the heat conduction equation and the linear transfer function resulting from the Laplace transform of the heat conduction equation, the second embodiment is similar to the first embodiment.

Whereas in the first embodiment, "gain" is a fixed value, in the second embodiment, "gain" is a variable value.

In other words, the SMA temperature estimation unit 34 according to the second embodiment acquires information about heater temperature at a heating start time at which the heater 22 starts heating the SMA pipe 21, which is the variable-rigidity member, and sets the gain based on the information about the heater temperature at the heating start time. Specifically, in setting the variable value of "gain," a table of heater temperature and a gain value such as shown in FIG. 4 is used.

Note that the table of the heater temperature and the gain value is assumed to be stored in the SMA temperature estimation unit 34 in the present embodiment, but may be stored in another storage unit of the control apparatus 3.

Note that when the surrounding environment temperature $T_e$ disperses, the gain to be set originally varies, and the heater temperature at the start of heating the SMA pipe 21 is heater temperature≈surrounding environment temperature $T_e$, and thus, in the present embodiment, the gain is set according to $T_e$ at the start of heating the SMA pipe 21.

Effect of Second Embodiment

As described above, the rigidity control apparatus according to the second embodiment achieves an effect similar to the effect of the first embodiment. In addition, by making "gain" a variable value using the table of the heater temperature and the gain value, the rigidity control apparatus according to the second embodiment can estimate the temperature of the shape-memory alloy member (SMA pipe 21), which is the variable-rigidity member, more accurately, and thus can further increase the accuracy of rigidity control over the SMA pipe 21.

Third Embodiment

Next, a third embodiment of the present invention will be described.

A rigidity control apparatus according to the third embodiment is similar to the first embodiment in a basic configuration, and thus only differences will be described here. Note that both in terms of the heat conduction equation and the linear transfer function resulting from the Laplace transform of the heat conduction equation, the third embodiment is similar to the first embodiment.

Whereas in the first embodiment. "time constant" is a fixed value, in the third embodiment, "time constant" is a variable value.

In other words, in the third embodiment, the control apparatus 3 is provided with a temperature history keeping unit (memory) configured to record temperature history information about the SMA pipe 21, and the SMA temperature estimation unit 34 sets the time constant based on the temperature history information. Specifically, in setting the variable value of "time constant," a table such as shown in FIG. 7 is used.

Figure 5:
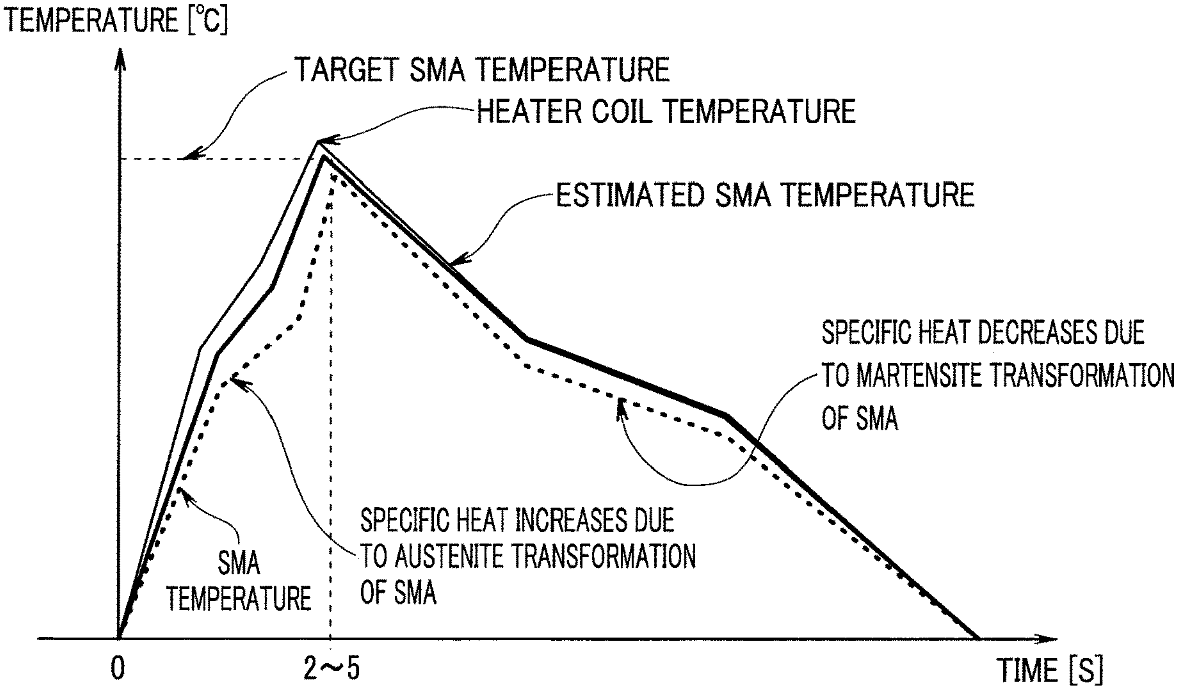
FIG. 5 is a graphical chart showing relationships among estimated temperature and target temperature of a shape-memory member, heater temperature, and temperature of the shape-memory member when a variable-rigidity member temperature estimation unit estimates the temperature of the shape-memory member in a rigidity control apparatus according to a third embodiment of the present invention.
Figure 6:
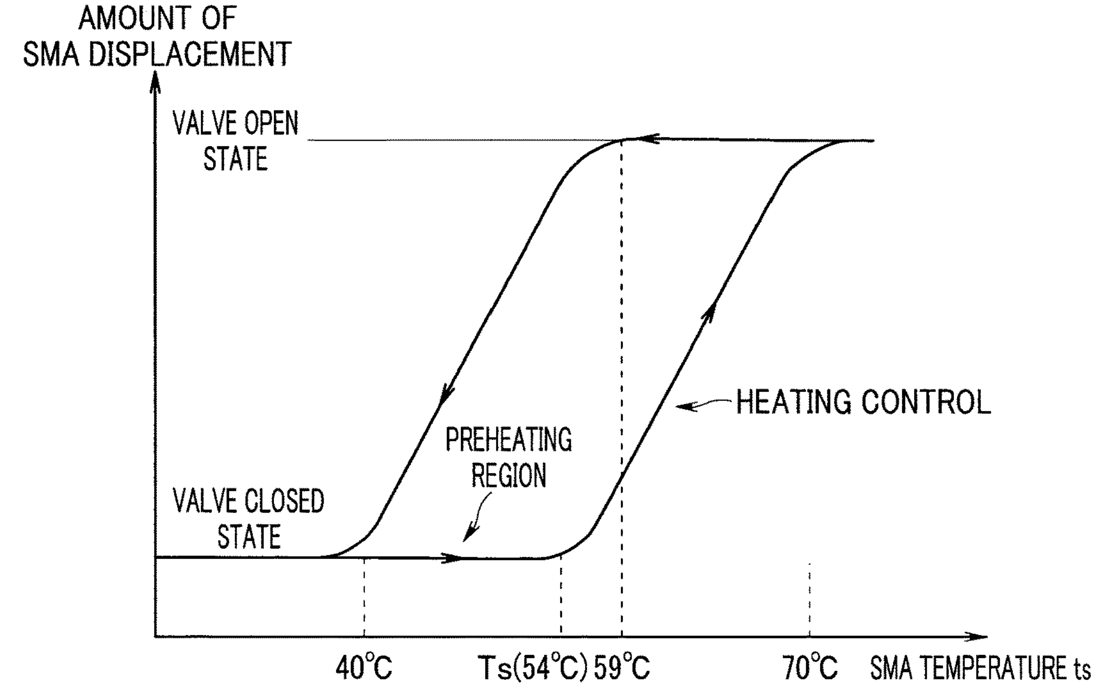
FIG. 6 is a diagram showing hysteresis characteristics of an amount of SMA displacement with respect to SMA temperature changes of a shape-memory member disposed in an endoscope insertion portion according to the third embodiment.

FIG. 5 is a graphical chart showing relationships among estimated temperature and target temperature of the shape-memory member, heater temperature, and temperature of the shape-memory member when the variable-rigidity member temperature estimation unit estimates the temperature of the shape-memory member in the rigidity control apparatus according to the third embodiment of the present invention, and FIG. 6 is a diagram showing hysteresis characteristics of an amount of SMA displacement with respect to SMA temperature changes of the shape-memory member disposed in an endoscope insertion portion according to the third embodiment.

Specific heat c of the SMA pipe 21 undergoes changes in value during transformation of the shape-memory alloy member of the SMA pipe 21 and has hysteresis, and thus, in the present embodiment, the specific heat c is set based on an SMA temperature history.

In other words, as shown in FIG. 5, the specific heat increases due to austenite transformation of SMA and decreases due to martensite transformation. As shown in FIG. 6, an amount of SMA displacement has predetermined hysteresis, and the specific heat has hysteresis as well.

Note that the temperature history keeping unit is assumed to be provided in the SMA temperature estimation unit 34 in the present embodiment, but may be provided in other part of the control apparatus 3.

Effect of Third Embodiment

As described above, the rigidity control apparatus according to the third embodiment achieves an effect similar to the effect of the first embodiment. In addition, by providing the temperature history keeping unit configured to record temperature history information about the SMA pipe 21, allowing the SMA temperature estimation unit 34 to set the time constant as a variable value based on the temperature history information, the rigidity control apparatus according to the third embodiment can estimate the temperature of the shape-memory alloy member (SMA pipe 21), which is the variable-rigidity member, more accurately, and thus can further increase the accuracy of rigidity control over the SMA pipe 21.

Fourth Embodiment

Next, a fourth embodiment of the present invention will be described.

A rigidity control apparatus according to the fourth embodiment is similar to the first embodiment in a basic configuration, and thus only differences will be described here. Note that both in terms of the heat conduction equation and the linear transfer function resulting from the Laplace transform of the heat conduction equation, the fourth embodiment is similar to the first embodiment.

Figure 8:
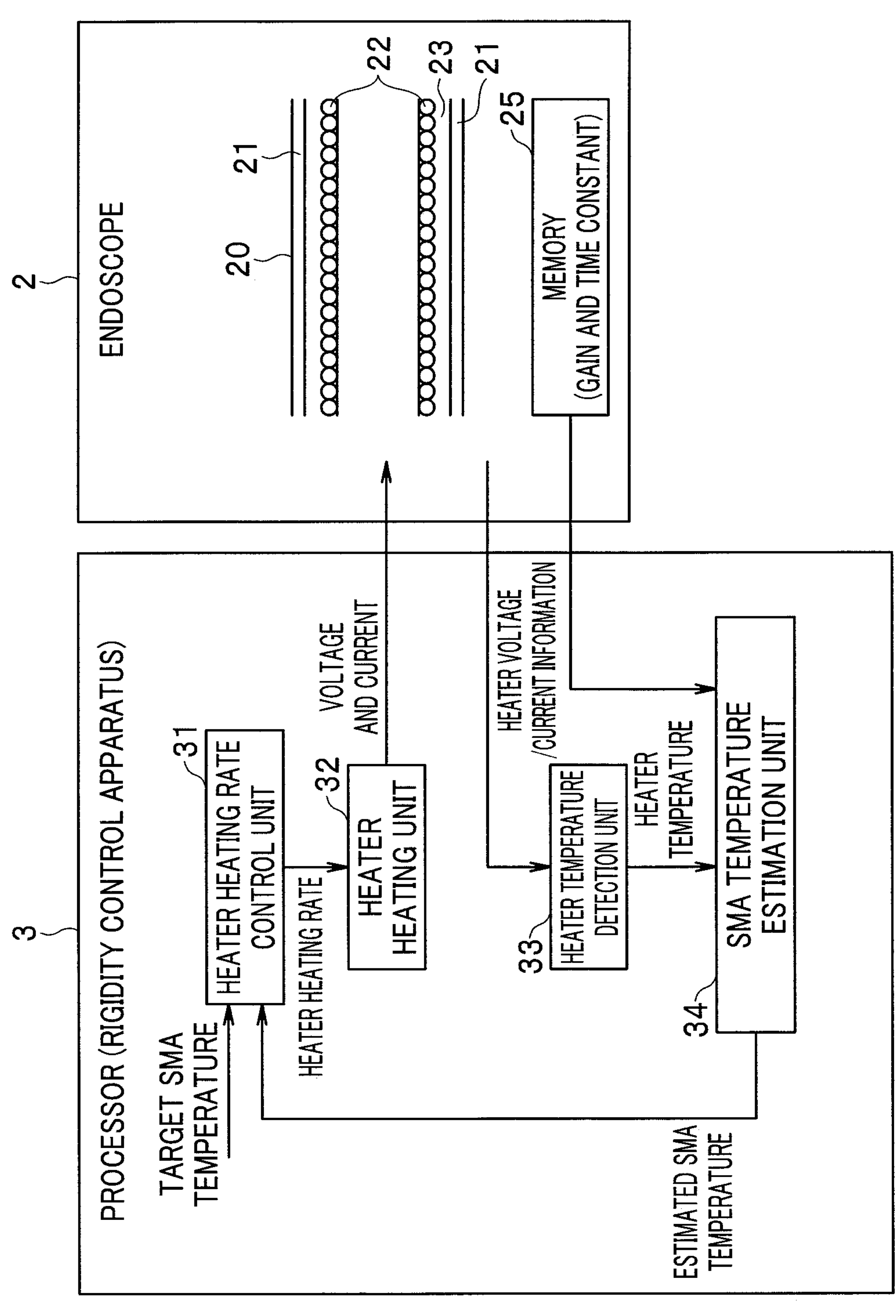
FIG. 8 is a block diagram showing a configuration of main part of a rigidity control apparatus according to a fourth embodiment of the present invention, and configurations of a variable-rigidity apparatus in an endoscope insertion portion and a memory unit.

FIG. 8 is a block diagram showing a configuration of main part of the rigidity control apparatus according to the fourth embodiment of the present invention, and configurations of a variable-rigidity apparatus in an endoscope insertion portion and a memory unit.

As shown in FIG. 8, the fourth embodiment is characterized in that information about "gain" and "time constant" set beforehand for each endoscope 2 is stored in a memory 25 of the endoscope 2. With the rigidity control apparatus according to the fourth embodiment, when a predetermined endoscope 2 is connected to the control apparatus 3, the SMA temperature estimation unit 34 of the control apparatus 3 acquires information (information about "gain" and "time constant" set beforehand) unique to the endoscope 2 from the memory 25 of the connected endoscope 2 and estimates the SMA temperature of the SMA pipe 21 from the temperature of the heater 22 based on the information about "gain" and "time constant."

Effect of Fourth Embodiment

As described above, the rigidity control apparatus according to the fourth embodiment achieves an effect similar to the effect of the first embodiment. Since information about "gain" and "time constant" set beforehand for each endoscope 2 is stored in the memory 25 of the endoscope 2 and the SMA temperature estimation unit 34 estimates the SMA temperature of the SMA pipe 21 from the temperature of the heater 22 based on the information about "gain" and "time constant" of the connected endoscope 2, even when multiple types of endoscope 2 are connected to a single control apparatus 3, which is the rigidity control apparatus, the SMA temperature of the SMA pipe 21 can be estimated precisely for each type of endoscope.

Here, the control apparatus 3 according to each of the embodiments described above includes, for example, a processor and a storage such as a memory. Different functions of the processor, for example, may be implemented by separate pieces of hardware. For example, the processor includes hardware, which can include at least one of a circuit that processes digital signals and a circuit that processes analog signals. For example, the processor can be made up of one or more circuit devices (e.g., ICs) or one or more circuit elements (e.g., resistors or capacitors) mounted on a circuit board. Various types of processor such as a CPU (central processing unit), a DSP (digital signal processor), a GPU (graphical processing unit), and a GSP (graphical streaming processor) are available for use. The processor may be a hardware circuit such as an ASIC (application specific integrated circuit) or an FPGA (field-programmable gate array). The processor may include an amplifier circuit or a filter circuit configured to process analog signals. The memory may be a semiconductor memory such as an SRAM or a DRAM; a register; or an optical storage device such as an optical disk device.

The present invention is not limited to the embodiments described above, and various changes and alterations are possible without departing from the gist of the invention.

What is claimed is:

1. A rigidity control apparatus comprising:

a processor comprising hardware and configured to control a variable-rigidity apparatus, the variable-rigidity apparatus including a variable-rigidity member, a flexural rigidity of the variable-rigidity apparatus increases when the variable-rigidity member is heated, and a heater separate from the variable-rigidity member and configured to generate heat upon being supplied with electric power and to thermally heat the variable-rigidity member, wherein the processor is further configured to:

calculate temperature information of the heater based on information obtained from the heater, and estimate temperature information of the variable-rigidity member based on the temperature information of the heater wherein the processor is configured to estimate the temperature information of the variable-rigidity member using a heat conduction model.

2. The rigidity control apparatus according to claim 1, wherein the processor is configured to output temperature information of the variable-rigidity member based on a function that uses the temperature information of the heater as an input value, the function including:

a gain representing a relationship between a temperature of the heater and a temperature of the variable-rigidity member, and a time constant representing a response characteristic of the variable-rigidity member to a temperature change caused by heating by the heater, wherein the function outputs the temperature information of the variable-rigidity member.

3. The rigidity control apparatus according to claim 2, wherein the processor is configured to acquire temperature information of the heater at a heating start time at which the heater starts heating the variable-rigidity member, and set the gain of the function based on the temperature information of the heater acquired at the heating start time.

4. The rigidity control apparatus according to claim 2, further comprising a memory configured to store temperature history information of the variable-rigidity member, wherein the processor is configured to set the time constant of the function based on the temperature history information stored in the memory.

5. The rigidity control apparatus according to claim 2, wherein the gain and the time constant are set as fixed values.

6. The rigidity control apparatus according to claim 1, wherein the processor is configured to control the heater based on the temperature information of the variable-rigidity member.

7. The rigidity control apparatus according to claim 1, wherein:

the heater is electrically conductive, and is configured to generate heat upon being supplied with electric power; and the processor is configured to calculate the temperature information of the heater based on information corresponding to a voltage applied to the heater and a current flowing through the heater.

8. The rigidity control apparatus according to claim 1, wherein:

the variable-rigidity member has a cylindrical shape;

a thermally conductive member is disposed between the heater and the variable-rigidity member and configured to thermally conduct heat from the heater to the variable-rigidity member; and the heater is disposed on an inner side of the thermally conductive member and is configured to heat the variable-rigidity member via the thermally conductive member.

9. The rigidity control apparatus according to claim 1, wherein the processor is configured to acquire temperature of the heater at a heating start time at which the heater starts heating the variable-rigidity member, and estimate the temperature information of the variable-rigidity member based on the temperature information of the heater and on the temperature information of the heater acquired at the heating start time.

10. The rigidity control apparatus according to claim 1, further comprising a memory configured to store temperature history information about the variable-rigidity member, wherein the processor is configured to estimate temperature information of the variable-rigidity member based on the temperature information of the heater and the temperature history information stored in the memory.

11. The rigidity control apparatus according to claim 1, wherein the processor is configured to:

acquire voltage information and current information corresponding to the heater;

acquire resistance information of the heater based on the acquired voltage information and current information; and calculate temperature information of the heater based on the resistance information.

12. The rigidity control apparatus according to claim 1, wherein the processor is configured to:

set a heat conduction equation shown below; and estimate the temperature information of the variable-rigidity member based on the heat conduction equation:

$$mc\frac{dT_{MSA}}{dt} = \frac{k_K A_k}{D_K}(T_{HEATER} - T_{SMA}) - \frac{k_s A_s}{D_s}(T_{SMA} - T_e)$$

wherein:

m is Mass of SMA [g], c is Specific heat of SMA [J/g/K],

TSMA is SMA temperature [K] (output value), t is time [s],

KK is Average thermal conductivity from heater coil to SMA (mainly conductive material), AK is Average surface area from heater coil to SMA (mainly conductive material), DK is Average thickness from heater coil to SMA (mainly conductive material), $T_{HEATER}$ is Heater temperature (input value), KS is Average thermal conductivity of surrounding environment of SMA (in-scope air space and in-scope components), AS is Surface area of SMA [m2], DS is Average thickness to surrounding environment of SMA (in-scope air space and in-scope components), Teis Temperature [K] of surrounding environment of SMA (in-scope air space and in-scope components).

13. The rigidity control apparatus according to claim 12, wherein the processor is configured to derive a linear transfer function from a Laplace transform of the heat conduction equation shown below and estimate the temperature information of the variable-rigidity member.

$$\frac{T_{SMA}}{T_{HEATER}} = \frac{\frac{k_K A_K}{D_K}}{\frac{k_K A_K}{D_K} + \frac{k_S A_S}{D_S}}\left(1 + \frac{T_e}{T_{HEATER}}\right) \times \frac{1}{1 + \frac{\mathrm{mc}}{\frac{k_K A_K}{D_K} + \frac{k_S A_S}{D_S}} s}$$

$$\text{Gain: } \frac{\frac{k_K A_K}{D_K}}{\frac{k_K A_K}{D_K} + \frac{k_S A_S}{D_S}}\left(1 + \frac{T_e}{T_{HEATER}}\right)$$

$$\text{Timeconstant: } \frac{\mathrm{mc}}{\frac{k_K A_K}{D_K} + \frac{k_S A_S}{D_S}} s$$

* * * * *